United States Patent [19]

Guyton

[11] 4,034,771
[45] July 12, 1977

[54] COATED DENTAL TEXTILE MATERIAL AND METHOD OF PREPARING AND USING THE SAME

[76] Inventor: William Cecil Guyton, 922 Porter Ave., Ocean Springs, Miss. 39564

[21] Appl. No.: 551,418

[22] Filed: Feb. 20, 1975

[51] Int. Cl.² .................................. A61C 15/00
[52] U.S. Cl. ........................................... 132/91
[58] Field of Search ............ 132/91, 89; 128/335.5; 428/267; 117/135.5, 161

[56] References Cited

U.S. PATENT DOCUMENTS

| | | | |
|---|---|---|---|
| 3,632,416 | 1/1972 | Shepherd | 128/335.5 |
| 3,830,246 | 8/1974 | Gillings | 132/89 |

Primary Examiner—G.E. McNeill
Attorney, Agent, or Firm—L. S. Van Landingham, Jr.

[57] ABSTRACT

Coated dental textile material is provided which has a fluorine-containing compound distributed through the coating and/or deposited thereon. The fluorine-containing compound provides fluoride ion in a therapeutic amount to inhibit the formation of dental caries when the coated dental textile material is intimately contacted with the teeth and gingiva to remove food deposits. A method of preparing the dental textile material is provided which assures that a proper amount of the fluorine-containing compound is substantially uniformly distributed through the coating and/or deposited thereon. A method of inhibiting the formation of dental caries is also provided wherein the coated dental textile material of the invention is used periodically to remove food deposits from the teeth and gingiva.

24 Claims, 1 Drawing Figure

U.S. Patent July 12, 1977 4,034,771
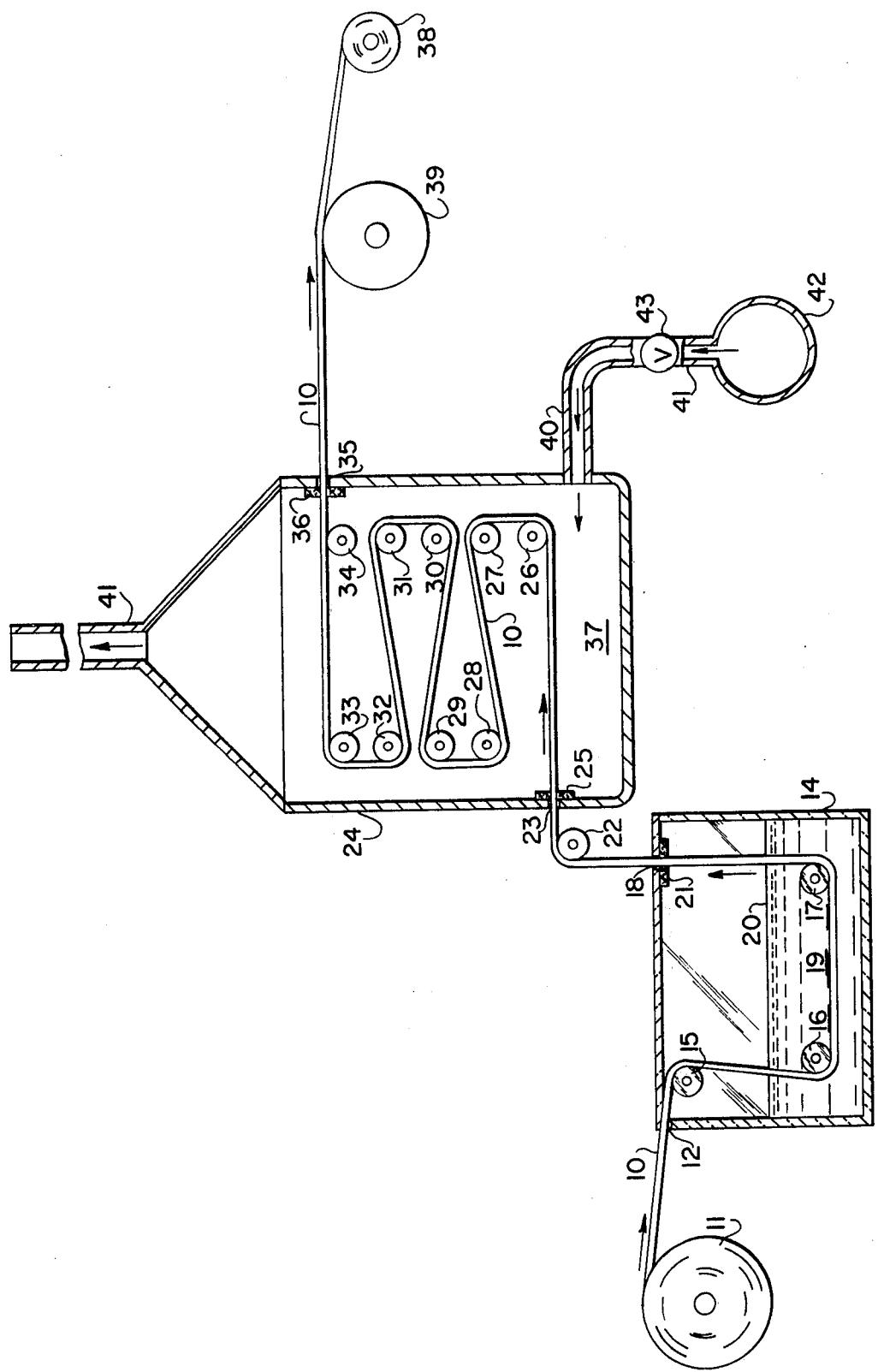

COATED DENTAL TEXTILE MATERIAL AND METHOD OF PREPARING AND USING THE SAME

THE BACKGROUND OF THE INVENTION

1. The Field of the Invention

The present invention broadly relates to dental textile materials. In one of its more specific variants, the invention is concerned with the application of a fluorine-containing compound to dental textile materials which provides fluoride ion to inhibit the formation of dental caries. The invention further relates to the dental textile material of the invention and the use thereof in inhibiting the formation of dental caries.

2. The Prior Art

Bacterial action of food deposits tends to cause disintegration and erosion of the dental surfaces and soreness and softening of the gums. This is especially pronounced in the more susceptible decay and inflammation areas such as the contact points of the teeth and at or immediately below the gingiva. Dental caries are one result of such baterial action, and inflammation of the gingiva is another.

Dental aids such as floss and tape have been used extensively heretofore for periodically removing food deposits from the teeth and gingiva. The prior art dental floss and tape may be waxed or uncoated, and it may be prepared from multistrand textile materials such as nylon or cotton. Whether waxed or uncoated, the prior art dental floss or tape was not provided with an entirely suitable substance which is effective to inhibit the formation of dental caries. As a result, while the prior art dental floss and tape performed the basic function of removing existing food deposits, it was not capable of preventing future food deposits from causing dental caries through fermentation and bacterial action prior to removal. Thus, the dental art has long sought an entirely satisfactory coated dental tape which is capable of not only removing food deposits from teeth and the gingiva, but which is also capable of effectively inhibiting the tendency toward future formation of dental caries.

THE SUMMARY OF THE INVENTION

The present invention provides an improved coated dental textile material which has the important additional benefit of inhibiting the formation of caries in the cleaned teeth, and especially at the most susceptible decay areas such as the contact points and near or beneath the gingiva. This is accomplished by providing a hydrophilic coating and/or a deposit thereon which releases fluoride ion in an amount effective to inhibit the formation of dental caries when the coated dental textile material is intimately contacted with the teeth and gingiva to remove food deposits. The improved coated dental textile material is preferably prepared by the novel method of the invention. The resultant coated dental textile material is especially useful in the novel method of the invention for inhibiting the formation of dental caries in teeth.

The accompanying drawing and the following detailed description of the invention, including the preferred variants and embodiments thereof, may be referred to for a more complete and comprehensive understanding of the invention.

BRIEF DESCRIPTION OF THE DRAWING

The single FIGURE of the drawing schematically illustrates one presently preferred arrangement of apparatus for applying a fluorine-containing compound to dental textile material.

THE DETAILED DESCRIPTION OF THE INVENTION INCLUDING CERTAIN PRESENTLY PREFERRED VARIANTS AND EMBODIMENTS THEREOF

Referring now to the drawing, a dental textile material 10 is fed from a master supply spool 11 through an opening 12 into tank 14. The textile material 10 then passes over roll 15 and downward under rolls 16 and 17 before being withdrawn upward from tank 14 via opening 18. The tank 14 is partially filled with coating liquid 19 which contains a fluorine compound to be described more fully hereinafter. The rolls 16 and 17 are submerged in the liquid 19, and thus the textile material 10 is coated or saturated therewith upon emerging from the liquid surface 20.

Excess liquid 19 is removed from the textile material 10 by felt wiper 21. Then the textile material which is coated or saturated with the liquid 19, is passed over roll 22 and through opening 23 into dryer 24. The opening 23 is provided with felt washer 25 to prevent excessive loss of the gaseous treating fluid from the interior 37 of dryer 24. The gaseous treating fluid may be hot air. The textile material 10 is passed through dryer 24 along a circuitous path defined by the arrangement of rollers 26, 27, 28, 29, 30, 31, 32, 33, and 34, and it is then withdrawn through opening 35. The felt washer 36 prevents excessive loss of the gaseous treating medium from the interior 37 of dryer 24. After passing through opening 35, as will be described more fully hereinafter, the textile material 10 has a solid coating and/or deposit thereon which contains the fluorine compound. The resultant coated dental textile material may be wound on consumer spools 38 or packaged in other suitable consumer dispensers in lengths controlled by photoelectric counting or measuring device 39.

The hot gaseous treating medium is supplied to the interior 37 of dryer 24 via conduit 40, and after passing upward in intimate contact with the textile material 10 to be treated, is then withdrawn via conduit 41. The hot gaseous treating medium is supplied to interior 37 by heater-blower 42 at a rate controlled by valve 43.

The supply spool 11 is preferably spring loaded for tension purposes, and the consumer spool 38 is preferably provided with prior art means (not shown) for rotating the same and thereby pulling the textile material 10 through tank 14 and dryer 24. The tension means for roll 11 and the driving means for roll 38 may be of conventional construction and design and are not shown in the interests of clarity and simplifying the drawing. The counter 39 likewise may be of conventional construction and design, and performs the function of allowing a predetermined length or amount of coated textile material 10 to be supplied to a plurality of sequentially positioned consumer spools 38 or other suitable consumer dispensers.

The basic textile material 10 to be treated initially may be any suitable prior art dental textile material but is preferably of indefinite length and composed of a plurality of elongated generally longitudinally extending textile fibers. Suitable materials for use in preparing the basic textile material 10 include naturally occurring textile fibers, such as cotton and flax, and synthetic textile fibers or filaments such as nylon and other polyamides, polyesters, and the like. Cotton is usually the preferred naturally occurring textile fiber, and nylon is usually the preferred synthetic textile fiber or filament. In all instances, it is usually preferred that the basic textile material 10 be composed of a plurality of individual generally longitudinally extending textile fibers or filaments. The textile fibers may be relatively short such as cotton fibers or continuous strands or filaments such as with nylon. Such plurality of fibers or multistrands may be loosely twisted if desired so as to assume a semi-thread to thread-like configuration. The basic dental textile material 10 to be treated initially may be in the form of uncoated conventional dental floss or tape. As a general rule, dental floss or tape prepared from a plurality of continuous nylon filaments or strands is preferred.

The tank 14, the dryer 24 and the rolls 16, 17, 22 and 26–34 may be constructed of prior art materials which are non-corrosive in liquid 19 and the gaseous treating medium in interior 37. For instance, the tank 14 may be glass lined and glass coated steel rolls 16, 17, 22 and 26–34 may be employed.

In accordance with one presently preferred variant of the invention, the dental textile material 10 has been precoated with an organic hydrophilic finish for textile materials and the coated surface thereof is highly hydrophilic in character. In such instances, the liquid 19 may be an aqueous solution of a fluorine compound. The fluorine compound may be present in an amount to provide about 0.001–10% by weight of fluoride ion, and preferably about 0.01–5% by weight of fluoride ion based upon the weight of the liquid 19. The best results are usually achieved when the fluorine compound is present in an amount to provide about 1.5–2% by weight of fluoride ion. The dental textile material 10 having the dry hydrophilic coating thereon is passed through the liquid 19 and is saturated with the aqueous fluorine compound. It is then withdrawn from the tank 14 and passed immediately through dryer 24 where the water content of the aqueous solution is removed very rapidly. The residence time within liquid 19 is very short and insufficient to result in the hydrophilic coating being removed to a substantial extent. Inasmuch as the surfaces of the textile fibers are hydrophilic, the liquid 19 immediately wets and penetrates the dental textile material 10 and saturates the same with the aqueous solution of the fluorine compound. Upon passing through dryer 24, the water content of the aqueous solution is removed leaving a dry hydrophilic coating on the textile fibers which in turn is coated with dry fluorine compound in the form of crystals and/or a dry film thereof. Thus, the resultant coated product has a highly hydrophilic surface which is wetted immediately by the saliva when used to clean the teeth, and the crystals and/or film of fluorine compound dissolves rapidly in the saliva at the points of contact. The fluoride ion that is released is available for treating the teeth in the precise areas where the need for treatment is greatest.

In accordance with another presently preferred variant of the invention, the dental textile material 10 has not received a precoating of an organic hydrophilic finish. In such instances, the liquid 19 may be an aqueous solution of the fluorine compound in the concentrations mentioned hereinbefore which also contains a hydrophilic organic finish for textile materials dissolved or dispersed therein. Upon passing the uncoated dental textile material 10 through tank 14, it is saturated with liquid 19, i.e., the hydrophilic organic finish which has the fluorine compound uniformly dispersed therein. The saturated dental textile material 10 is passed immediately through dryer 24 where the water content is removed rapidly. The final product is coated with a dry hydrophilic organic finish which has the fluorine substantially uniformly dispersed therein. The fluorine compound does not dissolve as rapidly in the saliva as in the aforementioned instance when the fluorine compound was deposited over the hydrophilic coating. However, the fluorine compound is released over a prolonged period of time and thus is ultimately effective in treating the teeth. This is especially true in instances where the hydrophilic coating containing the fluorine compound is partially removed from the textile fibers during use and particles thereof are deposited at the points of contact where the fluoride ion is needed to inhibit the formation of dental caries.

The hydrophilic finish may be present in the liquid 19 in the concentrations used to apply a coating thereof to textile materials in accordance with prior art practice. The concentration may be, for example, about 0.25–10% by weight and is preferably about 0.5–5% by weight in most instances. The resultant hydrophilic coating may be, for example, about 0.001–2% by weight and is preferably about 0.1–0.5% by weight based upon the weight of the dental textile material. The coating may have the fluorine compound substantially uniformly dispersed therein in an amount to provide, for example, about 0.0001–2% by weight of fluoride ion and preferably about 1–1.5% by weight of fluoride ion. Best results are usually achieved when the fluorine compound is present in an amount to provide about 1.25% by weight of fluoride ion.

In accordance with a further presently preferred variant of the invention, the dental textile material 10 may be precoated with a hydrophilic organic finish which has the fluorine compound substantially uniformly distributed therein as described above. In such instances, the precoated dental textile material 10 is passed through the tank 14 and is saturated with an aqueous solution of the fluorine compound following the same procedure as described hereinbefore for the variant wherein the dental textile material 10 is precoated with only the hydrophilic organic finish. Preferably the precoated dental textile material 10 is allowed to remain within the liquid 19 for the minimum period of time required to saturate the same with liquid 19, and it is then withdrawn immediately from tank 14 and rapidly dried in dryer 24. The resultant product has a dry coating of the hydrophilic organic finish with the fluorine compound substantially uniformly distributed therein and thereover a dry film and/or crystals of the fluorine compound. Thus, the final product of this variant combines the desirable properties of the two variants discussed hereinbefore. The fully exposed dry film and/or crystals of the fluorine compound dissolve rapidly in the saliva when the coated dental textile material is used to remove food particles from the teeth and gingiva. Thereafter the coating of the hydrophilic organic finish slowly releases fluoride ion over a prolonged period of time and especially in instances where the coating is of sufficient thickness to result in particles thereof being deposited on the contact points of the teeth and in the area of the gingiva. This combination of treatments, i.e., treatment with a relatively high concentration of fluoride ion immediately upon use followed by prolonged slow release of fluoride ion is especially effective in inhibiting the formation of dental caries.

Any suitable hydrophilic organic finish for textile materials may be used in practicing the present invention. Such materials are well known in the art and are commonly applied to textile materials for the purpose of enhancing the hydrophilic characteristics or properties of the textile fibers. The hydrophilic organic finish may be, for example, a soil release finish, an antistatic finish or a softening finish for textiles. Examples of hydrophilic organic finishes are disclosed in numerous United States patents including U.S. Pat. Nos. 3,384,506; 3,503,914; 3,509,048; 3,563,794; 3,592,686; 3,597,145; 3,620,826; 3,632,421; 3,782,898; 3,821,147 and 3,824,125, the disclosures of which are incorporated herein by reference.

Soil release finishes are usually preferred and especially hydrophilic soil release polymers which contain carboxylic acid groups in the free acid or neutralized form. Polymers of this type may be water soluble and thus may be dissolved in the aqueous treating solution, or they may be water swellable and water dispersible in the aqueous medium and especially when in the form of their ammonium and/or alkali metal salts. Soil release polymers of this type may be prepared from polymerizable unsaturated organic acids and the anhydrides thereof. The polymers may be homopolymers of the acid, or copolymers of the acid with one or more other ethylenically unsaturated monomers which are copolymerizable therewith. Specific examples of polymerizable acids include acrylic acid, methacrylic acid, maleic acid, fumaric acid, itaconic acid, crotonic acid, cinnamic acid and the like. Maleic anhydride is usually a preferred acid anhydride but other acid anhydrides may be used. Monomers copolymerizable therewith include esters of the foregoing acids prepared by reacting the acid with an alkyl alcohol containing, for example, 1–8 and preferably 1–4 carbon atoms, such as methyl, ethyl, propyl, isopropyl, n-butyl and isobutyl acrylate, methacrylate, fumarate, maleate, crotonate and cinnamate, acrylonitrile, and ethylenically unsaturated alcohols such as allyl alcohol and homologues thereof preferably containing up to about 10 carbon atoms.

Preferred polymers include polyacrylic acid, copolymers of acrylic acid and maleic anhydride, copolymers of acrylic acid, n-butyl acrylate and allyl alcohol, copolymers of acrylic acid and n-butyl acrylate, copolymers of methacrylic acid and ethyl acrylate, alginic acid, carboxymethyl cellulose including both low and high substitutions, admixtures of polyacrylic acid with copolymers of acrylic acid, n-butyl acrylate and allyl alcohol, admixtures of polyacrylic acid with copolymers of methyl acrylic acid and ethyl acrylate, and copolymers of methyl vinyl ether and maleic anhydride. Admixtures of two or more of the foregoing polymers may produce the best results in many instances.

The polymers may contain a high percentage of carboxylic acid groups. As a general rule, the polymers may contain more than 20% of the ethylenically unsaturated acid in polymerized form, and preferably more than 50%. Homopolymers of ethylenically unsaturated acids such as acrylic acid and methacrylic acid are very satisfactory and thus the ethylenically unsaturated acid may be present in amounts up to 100%. In instances where copolymers are prepared, usually the ethylenically unsaturated acid should be present in an amount of about 40–60%. The resulting polymers may be water soluble or water insoluble and are capable of being deposited on the surfaces of the textile fibers from aqueous media and preferably from an alkaline aqueous medium. The molecular weight is usually less than 50,000 and is preferably about 10,000–30,000 for the water soluble polymers, but may be much higher for the water insoluble polymers such as up to 800,000–2,000,000.

The hydrophilic organic finish may be applied to the dental textile material following conventional prior art practices. In stances where it is a soil release finish, and the soil release polymer is water soluble, then the dental textile material is merely immersed in an aqueous solution of the soil release polymer, followed by drying to produce a hydrophilic coating thereon. In stances where the polymer is essentially water insoluble but still water dispersible, then usually it is preferred that the polymer be in the neutralized form or an emulsion thereof may be used. In instances where an aqueous emulsion is used, then the emulsion may be prepared in accordance with prior art practices. Suitable emulsifying agents include the alkali metal salts of fatty acids, synthetic nonionic surfactants and anionic surfactants. As a general rule, the emulsion may be prepared by vigorously agitating the hydrophilic organic finish with approximately 1–10 and preferably 1–4 volumes of water in the presence of about 2–10% by weight of the emulsifying agent based upon the weight of the hydrophilic organic finish.

In instances where the fluorine compound is distributed in the coating of the hydrophilic organic finish, then the fluorine compound is present in a therapeutic amount to provide sufficient fluoride ion to inhibit the formation of dental caries when the coated dental textile material is intimately contacted with the teeth and gingiva to remove food deposits. While the concentration of the fluorine compound may vary over wide ranges, usually it is present in an amount to provide about 0.0001–2% by weight of fluoride ion, and preferably in an amount to provide about 1–1.5% by weight of fluoride ion. The best results are usually achieved at a concentration which provides approximately 1.25% by weight of fluoride ion. In instances where the fluorine compound is applied over the hydrophilic organic finish, then the concentrations thereof may be as set out above. The foregoing concentrations of fluorine ion are based upon the weight of the hydrophilic organic finish.

The liquid 19 may contain the fluorine compound in amounts to provide the ranges in the coating set out above. Usually the fluorine compound is present in liquid 19 in an amount to provide about 0.001–10% by weight of fluoride ion, and preferably in an amount to provide about 0.01–5% by weight of fluoride ion based upon the weight of the liquid 19. The results are usually achieved when the fluorine compound is present in an amount to provide about 1.5–2% by weight of fluoride ion.

The weight of the hydrophilic organic finish that is applied to the dental textile material may be in accordance with the prior art practices. Usually it is present in an amount of about 0.001–5% by weight, and preferably about 0.1–2% by weight based upon the weight of the textile material. However, much smaller or larger quantities may be applied when desired. In such instances, larger amounts such as 6-10% are preferred since the resultant hydrophilic coating may be removed more easily from the dental textile material during use and the fluorine compound carried thereby is available for treatment of the teeth.

The dryer 24 is operated at an elevated temperature which results in the rapid evaporation of the water content of the saturated dental textile material. The temperature may be, for example, about 150°-250° F and preferably about 200°-225° F. For best results, the saturated dental textile material 10 is removed rapidly from tank 14 and immediately flash dried in dryer 24. This results in a substantially uniform distribution of the fluorine compound.

In practicing the method of the invention for inhibiting the formation of dental caries, the resultant coated dental textile material may be used following prior art practices for the removal of food deposits from the teeth and gingiva. It is only necessary that the dental textile material of the invention be substituted for that normally used for this purpose. The intimate contact between the coated dental textile material and the teeth and gingiva results in the deposition of a therapeutic amount of the fluoride compound on the teeth which in turn inhibits the formation of dental caries. Inasmuch as the surface of the dental textile material is hydrophilic in character, it is readily wetted by the saliva and the fluorine compound rapidly dissolves therein at the point of use and thus is available in the areas of greatest need. Additionally, the coating of the hydrophilic organic finish may be removed to some extent and thus in instances where the fluorine containing compound is present therein, is available for slow release of fluoride ion. Frictional heat is often generated in instances where the dental floss or tape is pulled vigorously over the teeth and especially between the teeth at the points of contact. In such instances, the therapeutic effects of the fluoride ion that is released are surprisingly pronounced and dental caries are reduced very markedly.

Any suitable fluorine compound may be used in practicing the present invention provided it releases a therapeutic amount of fluoride ion to inhibit the formation of dental caries when the coated dental textile material is intimately contacted with the teeth and gingiva to remove food deposits. Examples of fluorine compounds which release fluoride ion include sodium fluoride, potassium fluoride, ammonium acid fluoride, iron fluoride, stannic fluoride and stannous fluoride. Stannous fluoride is usually much preferred over the remaining fluorides.

The foregoing detailed description and the following specific examples are for purposes of illustration only, and are not limiting to the spirit or scope of the appended claims.

EXAMPLE I

Water soluble polyacrylic acid having a molecular weight of approximately 20,000 is added to water in an amount of 2% by weight. The polymer is then neutralized by addition of sodium hydroxide solution while agitating the admixture to thereby convert the free carboxylic acid groups to the corresponding sodium salt. Thereafter stannous fluoride in an amount of 1.5-2% by weight based upon the weight of the solution is added and dissolved therein.

The resultant solution of polyacrylic acid and stannous fluoride is charged to a glass lined tank provided with submerged glass rolls similar to that illustrated in the drawings. Uncoated cotton dental floss of indefinite length is withdrawn from a master supply spool and passed under the submerged rolls and through the solution. Thereafter, the saturated cotton dental floss is withdrawn from the tank and passed through a dryer. The dryer is operated at a temperature of approximately 225° F. and the water content of the solution is flash evaporated from the saturated fibers of the dental floss.

The resultant dental floss having a solid hydrophilic coating of the polyacrylic acid thereon which contains the stannous fluoride substantially uniformly distributed therethrough is withdrawn from the dryer and wound on small consumer type spools using a photoelectric counter or measuring device to assure that each spool receives the desired length of dental floss. The filled spools of dental floss are packaged and stored awaiting use.

Upon testing the coated dental floss for removing food particles and deposits from the teeth and gingiva, it is noted that the hydrophilic coating is wetted immediately by the saliva and the fluoride compound is dissolved therein thereby releasing fluoride ion at points of contact with the teeth. Thus, the coating provides a source of fluoride ion for treatment of the teeth while the teeth are being cleaned with the dental floss, and the fluoride ion is deposited in areas where dental cavities are most likely to occur in the future.

EXAMPLE II

A hydrophilic copolymer of acrylic acid and ethyl acrylate containing equal mole porportions of the two polymerized monomers and having a molecular weight of about 800,000 is added to water in an amount of 2% by by weight. The copolymer is water insoluble initially but is water dispersible upon neutralizing to a pH of 7 with sodium hydroxide solution to convert the carboxylic acid groups to the corresponding sodium salt and agitating vigorously.

The resultant dispersion of the copolymer is charged to a glass lined tank provided with submerged glass coated rolls similar to that illustrated in the drawings. Uncoated multistrand nylon dental floss of indefinite length is withdrawn from a master supply spool and is passed under the submerged rolls and through the dispersion of copolymer. Thereafter, the saturated nylon dental floss is withdrawn from the tank and passed through a dryer which is operated at a temperature of approximately 225° F. Under these conditions, the water content of the copolymer dispersion is flash evaporated and a solid dry hydrophilic coating of the copolymer is produced on the strands of the nylon dental floss. Thus, the initially highly hydrophobic nylon filaments now have hydrophilic surfaces which are easily wetted by aqueous solutions. The resultant coated nylon dental floss is wound onto a master supply spool for further treatment with an aqueous solution of fluoride ion.

An aqueous solution is prepared containing 1.5-2% by weight of stannous fluoride. The stannous fluoride solution is charged to a glass lined tank provided with submerged glass coated rolls similar to that illustrated in the drawings. The coated multistrand nylon dental floss prepared as described above and having a hydrophilic surface on the nylon strands is withdrawn from the master supply spool and is passed through the stannous fluoride solution. Thereafter the saturated coated nylon dental floos is withdrawn from the tank and is passed through a dryer which is operated at 225° F. The water content of the stannous fluoride solution is flash evaporated to thereby deposit a film and/or crystals of stannous fluoride over the hydrophilic coating on the nylon filaments.

The resultant nylon dental floss is withdrawn from the dryer and thereafter packaged following the general procedure outlined in Example I. Microscopic examination of the coated dental floss indicates that the stannous fluoride is deposited over the hydrophilic coating and thus is readily available for dissolving in the saliva during use to remove food deposits from the teeth and gingiva.

EXAMPLE III

The general procedure of Example II is repeated with the exception of also dissolving stannous fluoride in the aqueous dispersion of the copolymer in an amount of 1.5–2% by weight based upon the weight of the solution. The nylon dental floss is saturated with the resultant dispersion and dried immediately to produce a solid dry hydrophilic coating of the copolymer on the nylon filaments which contains the stannous fluoride substantially uniformly dispersed therein.

The coated nylon dental floss thus produced is further treated with an aqueous solution containing 1.5–2% by weight of stannous fluoride following the general procedure of Example II. The resultant nylon dental floss has a dry hydrophilic coating of the copolymer with stannous fluoride dispersed therein in combination with a film and/or crystals of stannous fluoride thereover. Microscopic examination of the coated dental floss indicates that the stannous fluoride is deposited over the hydrophilic coating of the copolymer and thus is readily available for dissolving in the saliva during use to remove food deposits from the teeth and gingiva. In addition thereto, a portion of the hydrophilic coating may be removed during use to thereby provide prolonged release of the fluoride ion in the areas where it is needed most for treatment of the teeth.

EXAMPLE IV

This example illustrates the use of the coated dental products of the invention in the treatment of patients to inhibit the formation of dental caries.

The patients are divided into two groups and identified as group A and group B. Group A is further divided into three subgroups, i.e., subgroup A-1, subgroup A-2 and subgroup A-3. Subgroups A-1, A-2 and A-3 are given samples of the coated dental floss produced by experiments I, II and III, respectively, and instructed in the proper use thereof to remove food particles from the teeth and gingiva. Group B is similarly instructed but provided with conventional waxed dental floss which does not contain a fluorine compound.

The two groups are examined periodically at three month intervals and the rate of formation of dental caries is noted. The three subgroups using the dental floss of the invention, i.e., subgroups A-1, A-2 and A-3 have markedly fewer dental caries than the control Group B using the waxed dental floss of the prior art which does not contain the fluorine compound. Thus, the coated dental floss of the invention is effective in inhibiting the formation of dental caries.

I claim:

1. A method of preparing coated dental textile material for use in removing food deposits from the teeth and gingiva comprising applying an aqueous solution of a fluorine-containing compound to dental textile material, the dental textile material having a coating of an organic hydrophilic finish for textile material thereon and the coated surface thereof being hydrophilic in character, the said fluorine-containing compound being present in the aqueous solution in an amount to provide about 0.001–10% by weight of fluoride ion based upon the weight of the aqueous solution, and thereafter rapidly drying the dental textile material to produce a dry hydrophilic coating on the dental textile material which has dry fluorine-containing compound thereon, the fluorine-containing compound providing fluoride ion in a therapeutic amount to inhibit the formation of dental caries when the resultant coated dental textile material is intimately contacted with the teeth and gingiva to remove food deposits therefrom.

2. The method of claim 1 wherein the fluorine-containing compound comprises stannous fluoride.

3. The method of claim 1 wherein the dental textile material comprises a plurality of generally longitudinally extending nylon filaments, the nylon filaments being hydrophobic in character initially and the surface thereof being rendered hydrophilic by the said coating of organic hydrophilic finish, and the fluorine-containing compound is present in the aqueous solution in an amount to provide about 0.001–10% by weight of fluoride ion based upon the weight of the aqueous solution.

4. A method of preparing coated dental textile material for use in removing food deposits from the teeth and gingiva comprising applying an aqueous medium containing an organic hydrophilic finish for textile materials and a dissolved fluorine-containing compound to dental textile material, the said fluorine-containing compound being present in the aqueous medium in an amount to provide about 0.001–10% by weight of fluoride ion based upon the weight of the aqueous medium, and thereafter rapidly drying the dental textile material to produce an organic hydrophilic coating thereon which has the fluorine-containing compound substantially uniformly distributed therein, the fluorine-containing compound providing fluoride ion in a therapeutic amount to inhibit the formation of dental caries when the resultant coated dental textile material is intimately contacted with the teeth and gingiva to remove food deposits therefrom.

5. The method of claim 4 wherein the fluorine-containing compound comprises stannous fluoride.

6. The method of claim 4 wherein the fluorine-containing compound comprises stannous fluoride and the stannous fluoride is present in the aqueous solution in an amount to provide about 1.5–2% by weight of fluoride ion based upon the weight of the aqueous solution.

7. A method of preparing coated dental textile material for use in removing food deposits from the teeth and gingiva comprising applying an aqueous medium containing an organic hydrophilic finish for textile materials to dental textile material, thereafter rapidly drying the dental textile material at an elevated temperature to evaporate the water from the aqueous medium and produce a dry coating thereon of the organic hydrophilic finish, the surface of the resultant coated dental textile material being hydrophilic in character, applying an aqueous solution containing a fluorine compound which provides fluoride ion to the hydrophilic surface of the coated dental textile material, the said fluorine-containing compound being present in the aqueous solution in an amount to provide about 0.001–10% by weight of fluoride ion based upon the weight of the aqueous solution, and thereafter rapidly drying the dental textile material to produce a dry hydrophilic coating on the dental textile material which has dry fluorine-containing compound thereon, the fluorine-containing compound providing fluoride ion in a therapeutic amount to inhibit the formation of dental caries when the resultant coated dental textile material is intimately contacted with the teeth and gingiva to remove food deposits therefrom.

8. The method of claim 7 wherein the said fluorine-containing compound comprises stannous fluoride.

9. The method of claim 7 wherein the aqueous medium containing the organic hydrophilic finish has a fluorine-containing compound dissolved therein, and the said coating of the organic hydrophilic finish has the fluorine-containing compound substantially uniformly distributed therein to thereby provide additional fluoride ion when the dental textile material is intimately contacted with the teeth and gingiva.

10. The method of claim 7 wherein the dental textile material comprises a plurality of generally longitudinally extending nylon filaments, the nylon filaments being hydrophobic in character initially and the surface thereof being rendered hydrophilic by the said coating of organic hydrophilic finish.

11. An elongated coated dental textile material for use in removing food deposits from the teeth and gingiva comprising a plurality of elongated generally longitudinally extending textile fibers coated with an organic hydrophilic finish for textile materials, the said coating of organic hydrophilic finish having a fluorine-containing compound substantially uniformly distributed therein, the fluorine-containing compound being present in an amount to provide about 0.0001–2% by weight of fluoride ion based upon the weight of the said coating of organic hydrophilic finish, and the fluorine-containing compound providing fluoride ion in a therapeutic amount to inhibit the formation of dental caries when the coated dental textile material is intimately contacted with the teeth and gingiva to remove food deposits therefrom.

12. The coated dental textile material of claim 11 wherein the fluorine-containing compound comprises stannous fluoride.

13. The coated dental textile material of claim 11 wherein the said coating of organic hydrophilic finish is water soluble whereby a portion thereof including the fluorine-compound therein is removed by the saliva when the dental textile material is intimately contacted with the teeth and gingiva.

14. An elongated coated dental textile material for use in removing food deposits from the teeth and gingiva comprising a plurality of elongated generally longitudinally extending textile fibers coated with an organic hydrophilic finish for textile materials, the said coating of organic hydrophilic finish having a fluorine-containing compound deposited thereon, the fluorine-containing compound being present in an amount to provide about 0.0001–2% by weight of fluoride ion based upon the weight of the said coating of organic hydrophilic finish, and the fluorine-containing compound providing fluoride ion in a therapeutic amount to inhibit the formation of dental caries when the coated dental textile material is intimately contacted with the teeth and gingiva to remove food deposits therefrom.

15. The coated dental textile material of claim 14 wherein the fluorine-containing compound comprises stannous fluoride.

16. The coated dental textile material of claim 14 wherein the said coating of organic hydrophilic finish is substantially water insoluble and has a fluorine-containing compound substantially uniformly distributed therein to thereby provide additional fluoride ion when the dental textile material is intimately contacted with the teeth and gingiva, the said additional fluoride ion being released at a relatively slow rate as compared with the rate of release of fluoride ion from the fluorine-containing compound deposited on the said coating of organic hydrophilic finish.

17. The coated dental textile material of claim 14 wherein the textile fibers comprise a plurality of nylon filaments.

18. The coated dental textile material of claim 17 wherein the said coating of organic hydrophilic finish is substantially water insoluble and has a fluorine-containing compound substantially uniformly distributed therein to thereby provide additional fluoride ion when the dental textile material is intimately contacted with the teeth and gingiva, the said additional fluoride ion being released at a relatively slow rate as compared with the rate of release of fluoride ion from the fluorine-containing compound deposited on the said coating of organic hydrophilic finish, and the fluorine-containing compound contains stannous fluoride.

19. A method of inhibiting the formation of dental caries in teeth comprising cleaning the teeth at periodic intervals with an elongated coated dental textile material to remove food deposits from the teeth and gingiva, the dental textile material being coated with a dry coating of an organic hydrophilic finish for textile materials, the said coating of organic hydrophilic finish having a fluorine-containing compound substantially uniformly distributed therein providing fluorine ion in a therapeutic amount to inhibit the formation of dental caries when the coated dental textile material is intimately contacted with the teeth and gingiva to remove food deposits therefrom, and the fluorine-containing compound being present in an amount to provide about 0.0001–2% by weight of fluoride ion based upon the weight of the said coating of organic hydrophilic finish.

20. The method of claim 19 wherein the fluorine-containing compound comprises stannous fluoride.

21. The method of claim 19 wherein the fluorine-containing compound is stannous fluoride, the said coating of organic hydrophilic finish also has dry stannous fluoride on the surface thereof, and the stannous fluoride is present in and on the said coating of organic hydrophilic finish in an amount to provide about 1–1.5% by weight of fluoride ion based upon the weight of the organic hydrophilic finish.

22. A method of inhibiting the formation of dental caries in teeth comprising cleaning the teeth at periodic intervals with an elongated coated dental textile material to remove food deposits from the teeth and gingiva, the dental textile material comprising a plurality of elongated generally longitudinally extending textile fibers and the textile fibers being coated with a dry coating of an organic hydrophilic finish for textile materials, the said coating of organic hydrophilic finish having a dry fluorine-containing compound on the surface thereof providing fluoride ion in a therapeutic amount to inhibit the formation of dental caries when the coated dental textile material is intimately contacted with the teeth and gingiva to remove food deposits therefrom, and the fluorine-containing compound being present in an amount to provide about 0.0001–2% by weight of fluoride ion based upon the weight of the said coating of organic hydrophilic finish.

23. The method of claim 22 wherein the fluorine-containing compound is stannous fluoride.

24. The method of claim 22 wherein the plurality of textile fibers comprises a plurality of nylon filaments which are initially hydrophobic in character and the surfaces thereof are rendered hydrophilic by the said coating of organic hydrophilic finish.

* * * * *